United States Patent [19]

Sonenberg et al.

[11] 4,056,520
[45] Nov. 1, 1977

[54] CLINICALLY ACTIVE BOVINE GROWTH HORMONE FRACTION

[75] Inventors: Martin Sonenberg, New York, N.Y.; Nobuyuki Yamasaki, Matsuyama, Japan

[73] Assignee: Research Corporation, New York, N.Y.

[21] Appl. No.: 573,902

[22] Filed: May 2, 1975

Related U.S. Application Data

[62] Division of Ser. No. 240,301, March 31, 1972, Pat. No. 3,904,753, which is a division of Ser. No. 13,162, Feb. 20, 1970, Pat. No. 3,664,925.

[51] Int. Cl.$^2$ .................... C07C 103/52; A61K 37/00
[52] U.S. Cl. ...................... 260/112.5 R; 260/112 R; 424/177
[58] Field of Search .................... 260/112.5 R, 112 R; 424/177

[56] References Cited

U.S. PATENT DOCUMENTS 3,317,400  5/1967  Reusser .............................. 424/177

OTHER PUBLICATIONS

Sonenberg et al.; Ann. N.Y. Acad. Sci., 148(2), 532–558 (1968).

*Primary Examiner*—Delbert R. Phillips

*Attorney, Agent, or Firm*—Cooper, Dunham, Clark, Griffin & Moran

[57] ABSTRACT

A clinically active component (TBGH-d) of a tryptic digest of bovine growth hormone (BGH) found to be homogeneous by disc electrophoresis and sedimentation equilibrium and having substantially the same molecular weight and amino acid composition as BGH was separated into two fractions, A-I and A-II, by dextran gel filtration in 50% acetic acid. The amino acid analysis of the A-I and A-II fractions accounted for all the amino acids in the TBGH-d. The biological activity of the A-II fraction was found to be about 10–30% of TBGH-d. This fraction, having a molecular weight of about 5000 and an amino acid content or chain length of 38 amino acids, appears to exhibit human growth hormone-like activity. This fraction also appears to have wider applicability than simply being useful for the acceleration of somatic growth in humans. For example, this fraction would appear to have utility in promoting increased function and growth in an impaired liver and in effecting tissue regeneration, such as the promotion of healing of stress ulcers. It would also appear that this fraction has utility in the stimulation of protein synthesis to increase immunological competence and in wound and fracture healing. Also, it would appear that this fraction has utility in non-human applications, e.g., for increasing milk production, for increasing wool production and for accelerating animal growth.

1 Claim, No Drawings

CLINICALLY ACTIVE BOVINE GROWTH HORMONE FRACTION

This is a division, of application Ser. No. 240,301 filed Mar. 31, 1972 of Martin Sonenberg and Nobuyuki Yamasaki, now U.S. Pat. No. 3,904,753 which in turn is a division of parent application Ser. No. 13,162 filed Feb. 20, 1970, now U.S. Pat. No. 3,664,925.

This invention relates to the production of clinically active growth hormone materials, particularly clinically active growth hormone materials derived from bovine growth hormone and the like.

It is known that fractions of tryptic digest of bovine growth hormone have human growth hormone-like activity in hypopituitary humans, see the articles by A. C. Nadler, M. Sonenberg, M. I. New and C. A. Free entitled "Growth Hormone Activity in Man with Components of Tryptic Digests of Bovine Growth Hormone" in *Metabolism* 16: No. 9, September, 830–845 (1967) and M. Sonenberg, C. A. Free, J. M. Dellacha, G. Bonadonna, A. Haymowitz and A. C. Nadler entitled "The Metabolic Effects in Man of Bovine Growth Hormone Digested with Trypsin" in *Metabolism* 14: No. 11, November, 1189–1213 (1965). Of further interest in connection with the preparation of growth hormone material from various sources including bovine pituitary growth hormone, see U.S. Pat. Nos. 2,974,088 (1961), 3,118,815 (1964), 3,265,578 (1966), 3,275,516 (1966), 3,306,823 (1967), 3,308,027 (1967) and 3,317,400 (1967). The disclosures of the above-identified publications and patents are herein incorporated and made part of this disclosure.

It is an object of this invention to provide clinically active hormone material derived from an animal source such as bovine growth hormone.

It is another object of this invention to provide a clinically active fraction derived from a tryptic digest of bovine growth hormone and method for producing same.

Another object of this invention is to provide growth hormone material useful for administering to animals and the like.

How these and other objects of this invention are achieved will become apparent in the light of the accompanying disclosure. In accordance with at least one embodiment of the practice of this invention at least one of the foregoing objects will be achieved.

A clinically active component TBGH-d of the tryptic digest of bovine growth hormone, homogeneous by sedimentation equilibrium and disc electrophoresis, was separated into two components of fractions, A-I and A-II, by dextran gel (Sephadex G-75) filtration in 50% acetic acid. The A-II fraction having a molecular weight of 5000 was found to possess a biological activity equivalent to 10-30% of TBGH-d.

This fraction made up of 38 amino acids exhibits human growth hormone-like activity as evidenced by a decrease in blood urea nitrogen and urinary nitrogen and an increase in serum inorganic phosphorus when administered to a pituitary dwarf. There was also observed an increase in urinary calcium. When human growth hormone was administered to the same pituitary dwarf the responses were qualitatively the same although the human growth hormone was more effective, as might be expected. This fraction in accordance with this invention evidencing clinical activity was administered by injection into the pituitary dwarf.

The clinically active fraction, the A-II fraction referred to hereinabove, upon analysis was found not to contain a disulfide bond and the amino terminal amino acid was found to be valine and the carboxyl terminal amino acid was found to be arginine.

The data obtained in connection with the preparation of the above-described A-II clinically active fraction indicate that the homogeneous hormonally active component of a tryptic digest of bovine growth hormone consists of two peptides formed by the cleavage of two peptide bonds at arginine residues within one of the disulfide groups and that these peptide groups are associated under mild conditions.

More particularly, in connection with the preparation of a clinically active fraction, the above-described A-II fraction in accordance with this invention, the clinically active component TBGH-d of the tryptic digest of bovine growth hormone homogeneous by sedimentation equilibrium and disc electrophoresis was separated into two components, A-I and A-II, by dextran gel (Sephadex G-75) filtration in 50% acetic acid. The molecular weight of the A-I fraction was found to be 16,000 and for the A-II fraction to be 5,000, as indicated hereinabove. The amino acid analysis of the A-I and A-II fractions accounted for the total amino acids in TBGH-d. Two disulfide bonds were found in the A-I fraction and none in the A-II fraction. Further, the amino terminal amino acids of the A-I fraction were found to be phenylalanine, alanine and serine and for the A-II fraction the amino terminal amino acid was found to be valine. The carboxyl terminal amino acids of the A-I fraction were phenylalanine and arginine and for the A-II fraction the carboxyl terminal amino acid was arginine.

The reduced and carboxymethylated A-I fraction gave two fractions by dextran gel filtration. The larger reduced and carboxymethylated peptide had a molecular weight of approximately 11,000 and contained phenylalanine and alanine as amino terminal residues and arginine as a carboxyl terminal amino acid. The molecular weight of the second reduced and carboxymethylated fraction was found to be approximately 5,000. In this second fraction serine was found to be the amino terminal amino acid and phenylalanine as the carboxyl terminal amino acid.

In the production of the clinically active A-II fraction one gram of bovine growth hormone BGH gave 920 milligrams of unfractionated tryptic digest of bovine growth hormone (TBGH). From this TBGH there was obtained 119 milligrams of component d of a tryptic digest of bovine growth hormone (TBGH-d) found to be clinically active. This amount of TBGH-d gave 84 mg. of the above-described A-I fraction and 28 mg. of the above-described clinically active A-II fraction.

In the preparation of the clinically active A-II fraction derived from a clinically active component TBGH-d of a tryptic digest of bovine growth hormone BGH, the BGH was prepared by the method of Dellachaand Sonenberg, see J. Biol. Chem. 239, 1515 (1964). The clinically active component TBGH-d was obtained by diethylaminoethyl (DEAE)cellulose column chromatography of the tryptic digest of BGH as reported in Ann, N.Y. Acad. Sci, 148, 532 (1968). In the preparation of the clinically active A-II fraction by dextran gel filtration the clinically active component TBGH-d of a tryptic digest of bovine growth hormone was added in 50% acetic acid to a column (2.5 × 40 cm.) of dextrane gel (Sephadex G-75) equilibrated with 50% (v/v) acetic acid at a temperature of 4° C., followed by elution with the same solution. Fractions eluted were read at 280 mu and an aliquot of each fraction was taken for further identification by ninhydrin reaction after alkaline hydrolysis, see J. Biol. Chem. 238 622 (1963). Fractions were evaporated and then freeze dried and the fractions were further purified by rechromatography. For the study of biological activity fractions obtained by gel filtration were freeze dried directly from 50% acetic acid. If desired, in the practice of this invention other solvents, such as urea, dioxane, dichloroacetic acid and acetic acid of higher or lower concentrations than 50% are useful in the practice of this invention for the preparation of the clinically active fraction.

In the preparation and the analyses of the materials in accordance with this invention, the analytical electrophoresis was carried out on polyacrylamide gel by the disc electrophoretic method of Ornstein, Ann. N.Y. Acad. Sci. 121, 321 (1964) and Davis, Ann. N.Y. Acad. Sci. 121, 404 (1964). The electrophoresis was performed at a pH of 9.5 in 7.5% polyacrylamide gel. Protein components were stained with 0.5% amidoschwarz in 7% acetic acid. For the amino acid analysis the proteins or peptides were hydrolyzed in 6N HCl at 110° C. under reduced pressure for 24 and 72 hours. Hydrolysates were analyzed on an amino acid analyzer according to the method of Spackman, Stein and Moore, Anal. Chem. 30, 1190 (1958) and corrections were applied for amino acids partially destroyed during hydrolysis.

In the determination of the $NH_2$-terminal residues, dinitrophenylation was performed without alcohol, J. Biol. Chem. 213, 487 (1955) at pH 8.6 at 40° C. for 3 hours. DNP-protein or -peptide was hydrolyzed by 6N HCl in a sealed evacuated tube at 105° C. for 16 hours. Identification and quantitative analysis of DNP-amino acids were performed by two-dimensional thin layer chromatography. Two solvent systems were used, solvent S1 made up of toluene/pyridine/ethylene chlorhydrin/0.8N ammonium hydroxide (100:30:60:60:) and solvent S2 made up of benzene/pyridine/acetic acid (80:20:2). The upper phase of solvent S1 was used for chromatography. DNP-spots were eluted with 4 ml. of 1% $NaHCO_3$ and their absorption read at 360 mu after removing silica gel by centrifugation. Pure DNP-amino acids were hydrolyzed with the samples followed by thin layer chromatography with the same procedure as that employed for DNP derivatives. The $NH_2$-terminal amino acid values were corrected for losses during these procedures.

For the determination of the COOH-terminal residues to 0.2 μmol of dried samples were added 25 mg. of hydrazine sulfate and the mixture was dried in a vacuum desiccator over $P_2O_5$ for 3 days. Anhydrous hydrazine (0.2ml) was added and allowed to react in a sealed tube at 60° for 16 hours. The hydrazinolysate was dried in a desiccator over concentrated $H_2SO_4$.

After treatment with heptanal, J. Biochem. (Tokyo) 68, 475 (1958), the hydrazinolysate was dinitrophenylated in 66% ethanol, Biochem. J. 39, 507 (1945), and the COOH-terminal DNP-amino acid fractionally extracted, J. Biochem. (Tokyo) 56, 314 (1964). Quantitative analysis of DNP-amino acids was performed by thin layer chromatography as described above for $NH_2$-terminal amino acids. Appropriate recovery corrections were determined by submitting given amino acids to the hydrazine reaction in the presence of protein.

Total reduction and carboxymethylation of TBGH-d or larger fractions obtained by gel filtration in 50% acetic acid were performed by the method of Crestfield et al, J. Biol. Chem. 238, 622 (1963). Fractionation of reduced and carboxymethylated peptides was carried out on a column (2.5 × 40 cm.) of dextran gel (Sephadex G-75) in 50% acid covered by aluminum foil. Aliquots of each fraction were taken for identification by the ninhydrin reaction. Peptide fractions were rotary evaporated and then freeze dried.

Molecular weights of TBGH-d fractions separated by gel filtration in 50% acetic acid were determined by sedimentation equilibrium at 4°-10° in a Spinco Model E ultracentrifuge equipped with ultraviolet optics and automatic scanner.

Growth hormone activity of TBGH-d as well as the fractions A-I and A-II obtained by gel filtration in 50% acetic acid was determined in hypophysectomized rats by the method of Marx, Simpson and Evans, Endocrinology 30, 1 (1942) and the weight gain for 10 days was recorded.

In the above mentioned preparation and/or analytical procedures, in the dextran gel filtration of the tryptic digest of bovine growth hormone the pure TBGH-d revealed a single peak on dextran gel Sephadex G-75 in 0.1 M carbonate buffer at ph 9.5. In 6 M urea, however, this component was separated into two peaks on Sephadex G-75. Upon elution of TBGH-d from the Sephadex G-75 column by means of 50% acetic acid the two fractions, A-I and A-II, were obtained with increasing elution volume, respectively.

In these procedures from 1 gm. of BGH the yield was 920 mg. of unfractioned TBGH, 119 mg. of homogeneous TBGH-d, 84 mg. of A-I and 28 mg. of A-II. Analytic disc electrophoresis revealed two homogeneous components A-I and A-II and component A-II had slightly greater anodal mobility than A-I.

In the molecular weight determination by sedimentation equilibrium the molecular weight of the large separated A-I fraction on Sephadex G-75 in 50% acetic acid was approximately 16,000 and that of the smaller A-II component was 5,000.

In the determination of the amino and carboxyl terminal amino acids of components A-I and A-II the number of moles of $NH_2$-terminal amino acids in component A-I was found to be 0.48 for phenylalanine, 0.44 for alanine and 0.83 for serine per mol of A-I molecular weight of 16,000. Valine was found as the $NH_2$-terminal amino acid of component A-II with 0.92 mol per mol of molecular weight of 5,000. Whereas TBGH-d had 1 phenylalanine and two arginine as the carboxyl terminal amino acids, component A-I had 1 mol of arginine and 1 mol of phenylalanine per molecular weight of 16,000. In contrast 1 mol of arginine was found in component A-II as a carboxyl terminal amino acid.

In accompanying Table No. 1 the amino acid analyses of components A-I and A-II are presented and compared with those of TBGH-d and BGH.

Table No. 1

| Amino Acid | BGH | TBGH-d | A-I | A-II |
|---|---|---|---|---|
| Lysine | 10.5 | 10.8 | 8.8 | 2.0 |
| Histidine | 3.0 | 3.4 | 3.2 | 0 |
| Arginine | 12.2 | 12.3 | 10.5 | 2.8 |
| Aspartic Acid and Asparagine | 15.1 | 15.4 | 10.8 | 3.8 |
| Threonine | 11.3 | 10.9 | 7.1 | 2.6 |
| Serine | 11.7 | 12.5 | 10.0 | 1.9 |
| Glutamic Acid and/or Glutamine | 21.6 | 21.7 | 18.1 | 4.9 |
| Proline | 6.1 | 5.9 | 5.9 | 0.9 |
| Glycine | 9.8 | 10.8 | 6.5 | 2.9 |
| Alanine | 13.5 | 12.6 | 12.1 | 1.0 |

Table No. 1-continued

| Amino Acid | BGH | TBGH-d | A-I | A-II |
|---|---|---|---|---|
| Cysteine (½) | 4.6 | 4.5 | 3.9 | 0 |
| Valine | 6.4 | 6.8 | 3.0 | 3.0 |
| Methionine | 4.4 | 4.2 | 2.3 | 1.0 |
| Isoleucine | 6.5 | 6.4 | 5.5 | 0.9 |
| Leucine | 24.3 | 23.9 | 19.5 | 5.1 |
| Tyrosine | 6.0 | 5.7 | 4.6 | 1.0 |
| Phenylalanine | 11.6 | 11.4 | 9.5 | 1.8 |

The tests of the biological activity of the growth hormone derivatives or components prepared in accordance with this invention are set forth in accompanying Table No. 2. As indicated by the results reported in accompanying Table No. 2 only component A-II prepared in accordance with this invention had growth promoting activity.

Table No. 2

| Fraction | Biological Activity (I.U./mg ± S.E.) |
|---|---|
| TBGH-d | 0.92 ± 0.19 |
| TBGH-d (50% acetic acid) | 0.095 |
| A-I | 0.075 |
| A-II | 0.34 ± 0.12 |

It was observed that the smaller peptide component A-II obtained from TBGH-d by dextran gel filtration in 50% acetic acid has approximately 30% of the biological activity of the parent material TBGH-d. It would appear that the active site of BGH may be present in a limited part of the whole protein molecule.

The clinically active component made in accordance with this invention may be administered to a human or to an animal parenterally, e.g. by intramuscular injection.

Although emphasis has been placed herein upon the preparation of the clinically active material from bovine growth hormone other animal growth hormone material would also appear to be suitable for the preparation therefrom of a clinically active component similar to or equivalent to the clinically active material derived from bovine growth hormone in accordance with this invention. Other such suitable animal growth hormone material would appear to include porcine growth hormone material and equine growth hormone material.

Techniques are known for obtaining a tryptic digest of bovine growth hormone (TBGH). In addition to the techniques already mentioned other suitable techniques are described in *Metabolism*, 14, 1189 (1965) and Metabolism, 16, 830 (1967). These other techniques may be employed in the preparation of TBGH in the practice of this invention.

Prior to the preparation of TBGH the bovine growth hormone (BGH) was prepared by the method described in J. Biol. Chem., 239, 1515 (1964). After preparation the BGH was then subjected to trypsin digestion to produce TBGH. The extent of proteolysis, yield and biological acitvity of the resulting digest TBGH are set forth in accompanying Table No. 3.

Table No. 3

| TBGH | Base Uptake Equivalents/22,000 g | Yield % | Biological Activity USP units/mg ± S.E. |
|---|---|---|---|
| 1 | 2.4 | 94 | 1.39 ± 0.20 |
|   |     |    | 1.29 ± 0.24 |
| 2 | 2.4 | 93 | 2.37 ± 0.32 |
|   |     |    | 1.68 ± 0.33 |
| 3 | 2.4 | 86 | 1.40 ± 0.32 |
| 4 | 2.4 | 85 | 1.50 ± 0.16 |
| 5 | 2.4 | 91 | 1.88 ± 0.44 |
| 6 | 2.5 | 98 | 1.16 ± 0.26 |

Table No. 3-continued

| TBGH | Base Uptake Equivalents/22,000 g | Yield % | Biological Activity USP units/mg ± S.E. |
|---|---|---|---|
| 7 | 2.5 | 93 | 1.79 ± 0.32 |

The resulting digest TBGH, as described hereinabove, is then subjected to fractionation by chromatography on diethylaminoethyl cellulose to produce the clinically active component TBGH-d found to be homogeneous by disc electrophoresis and sedimentation equilbrium. This component TBGH-d is then subjected to dextran gel filtration to produce the clinically active fraction A-II in accordance with this invention as described hereinabove.

In the treatment of the pituitary dwarf mentioned hereinabove with the active A-II fraction, the treatment involved metabolic studies. The pituitary dwarf received 5 milligrams of the A-II fraction dissolved in water twice a day intramuscularly for five days. The active A-II fraction could just as well been given intravenously although one would predict that the effects would be more prolonged with intramuscular injection. It would appear unlikely that the A-II fraction, being a peptide, could efficiently be given orally since it would be digested in the gastrointestinal tract.

Other tests involving the active A-II fraction prepared in accordance with this invention were also carried out. These tests involved studies in connection with isolated rat epidydimal fat pad tissues. The results of these tests indicate that the active A-II fraction is comparable in biochemical effects to bovine growth hormone and human growth hormone in the same tissues.

The following is an example in accordance with this invention for the preparation of the A-II active fraction:

EXAMPLE

Nine grams of bovine growth hormone prepared by the method of Dellacha and Sonenberg are digested at 25° C. at pH 9.5 in an automatic titrator under nitrogen with constant stirring. Purified trypsin is added to this bovine growth hormone which is in tenth molar KCl in a ratio of enzyme to bovine growth hormone of about 1:300. The digestion is allowed to proceed for about 8–12 minutes during which time two bonds are split. The reaction mixture is stopped by the addition of an equivalent amount of soybean trypsin inhibitor, e.g. about 3 milligrams, and the reaction mixture is transferred to dialysis tubing. It is dialyzed exhaustively against distilled water and then freeze-dried. From mine grams of undigested bovine growth hormone about 8½ grams of a total tryptic digest of bovine growth hormone are obtained. About four grams of the total digest are then applied to a DEAE-cellulose column and with stepwise elution with ammonium bicarbonate, concentrations 0.03 M, .05 M, 0.07 M, 0.1 M and 0.15 M successive fractions are obtained. The 0.05 M fraction generally contains the TBGH-d. From four grams of the total digest 450 milligrams of TBGH-d are obtained. This is recovered by freeze-drying directly. 200 milligrams of TBGH-d are then applied to a dextran gel (Sephadex G-75) column and developed with 50% acetic acid. Two fractions, A-I and A-II, are obtained. Both are recovered by freeze-drying directly from the acetic acid solution. From the 450 milligrams of TBGH-d about 100 milligrams of A-II are obtained. The A-II is then used directly for further chemical and biological studies. For human investigation the material is dissolved in water and acidified to pH 4.5. The A-II solution is then sterile-filtered through a Swinney filter to give a concentration of five milligrams/milliliter. This sterile solution is then used in animal tests for pyrogenicity, sterility and endotoxin contamination.

As will be apparent to those skilled in the art in the light of the foregoing disclosure, many modifications, substitutions and alterations are possible in the practice of this invention without departing from the spirit or scope thereof.

What is claimed is:

1. A polypeptide derivable from and being a fraction or moiety of bovine growth hormone and useful for the treatment of pituitary dwarfism, said polypeptide having a molecular weight of about 5000, an amino acid content or chain length of about 38 amino acids, said polypeptide recoverable by gel filtration in the present of 50% having valine as the amino terminal amino acid and arginine as the carboxyl terminal amino acid and having the amino acid analysis:

| | |
|---|---|
| lysine | 2.0 |
| arginine | 2.8 |
| asparatic acid and asparagine | 3.8 |
| threonine | 2.6 |
| serine | 1.9 |
| glutamic acid and/or glutamine | 4.9 |
| proline | 0.9 |
| glycine | 2.9 |
| alanine | 1.0 |
| valine | 3.0 |
| methionine | 1.0 |
| isoleucine | 0.9 |
| leucine | 5.1 |
| tyrosine | 1.0 |
| phenylalanine | 1.8 |

* * * * *

UNITED STATES PATENT AND TRADEMARK OFFICE
CERTIFICATE OF CORRECTION

PATENT NO. : 4,056,520
DATED : November 1, 1977
INVENTOR(S) : MARTIN SONENBERG and NOBUYUKI YAMASAKI It is certified that error appears in the above-identified patent and that said Letters Patent are hereby corrected as shown below:

Column 7, last line, after "50%" insert -- acetic acid --

Signed and Sealed this

Sixth Day of June 1978

[SEAL]

Attest:

RUTH C. MASON
*Attesting Officer*

DONALD W. BANNER
*Commissioner of Patents and Trademarks*